(12) United States Patent
Hamawaki

(10) Patent No.: US 7,989,503 B2
(45) Date of Patent: Aug. 2, 2011

(54) SMOOTH MUSCLE PERISTOLE INHIBITOR

(75) Inventor: Tomonori Hamawaki, Izumisano (JP)

(73) Assignee: Nihon Pharmaceutical Co., Ltd., Tokyo (JP)

( * ) Notice: Subject to any disclaimer, the term of this patent is extended or adjusted under 35 U.S.C. 154(b) by 1148 days.

(21) Appl. No.: 10/515,129

(22) PCT Filed: May 20, 2003

(86) PCT No.: PCT/JP03/06304
§ 371 (c)(1),
(2), (4) Date: Nov. 19, 2004

(87) PCT Pub. No.: WO03/097026
PCT Pub. Date: Nov. 27, 2003

(65) Prior Publication Data
US 2005/0239905 A1     Oct. 27, 2005

(30) Foreign Application Priority Data

May 22, 2002  (JP) .............................. 2002-147372
Dec. 27, 2002  (JP) .............................. 2002-379522

(51) Int. Cl.
*A61K 31/045* (2006.01)
(52) U.S. Cl. ........................................... 514/729
(58) Field of Classification Search .................. None
See application file for complete search history.

(56) References Cited

U.S. PATENT DOCUMENTS

| | | | | |
|---|---|---|---|---|
| 3,607,651 A | * | 9/1971 | Moroe et al. ................. | 435/280 |
| 4,816,247 A | * | 3/1989 | Desai et al. ................... | 514/216 |
| 5,364,632 A | * | 11/1994 | Benita et al. .................. | 424/450 |
| 5,559,157 A | * | 9/1996 | Kawashima et al. ......... | 514/777 |
| 5,925,365 A | * | 7/1999 | Yamamoto .................... | 424/401 |
| 6,126,954 A | * | 10/2000 | Tsaur ............................ | 424/401 |
| 2002/0012680 A1 | * | 1/2002 | Patel et al. .................... | 424/400 |
| 2002/0068092 A1 | * | 6/2002 | Bosch et al. .................. | 424/501 |
| 2003/0095990 A1 | * | 5/2003 | Hua et al. ..................... | 424/400 |
| 2003/0147927 A1 | * | 8/2003 | Khan et al. ................... | 424/400 |

FOREIGN PATENT DOCUMENTS

| | | |
|---|---|---|
| JP | 63-198634 | 8/1988 |
| WO | WO 00/42983 | * 7/2000 |

OTHER PUBLICATIONS

Nair, B: Final report on the safety assessment of mentha piperita (peppermint) oil, mentha piperita (peppermint) leaf extract, mentha peperita (peppermint) leaf, and mentha piperita (peppermint) leaf water. Int J Toxicol, 20 (suppl.3):61-73. 2001.*
Ros: Intestinal absorption of triglyceride and cholesterol. Dietary and pharmacological inhibition to reduce cardiovascular risk. atherosclerosis, 151:357-379, 2000.*
http://www.theherbarie.com/files/resource-center/formulating/Required_HLB_for_Oils_and_Lipids.pdf.*
J.M. Hills et al., The Mechanism of Action of Peppermint Oil on Gastrointestinal Smooth Muscle, Gastroenterology, 1991, vol. 101, No. 1, pp. 55-65.
T. Asao et al., "An easy method for the intraluminal administration of peppermint oil before colonoscopy and its effectiveness in reducing colonic spasm", Gastrointestinal Endoscopy, 2001, vol. 53, No. 2, pp. 172-177.

* cited by examiner

*Primary Examiner* — Jeffrey S Lundgren
*Assistant Examiner* — Bong-Sook Baek
(74) *Attorney, Agent, or Firm* — Wenderoth, Lind & Ponack, L.L.P.

(57) ABSTRACT

An emulsion comprising L-Menthol, a fat or oil and a surfactant wherein oil particles have an average diameter of 100 nm or less inhibits a content reduction attributed to, for example, evaporation of L-menthol, enhances a light transmission through liquid and is stable despite long-term storage. Thus, the emulsion can be appropriately used in the temporary inhibition of contraction of gastrointestinal tract for, for example, observation of gastrointestinal tract by an endoscope. This emulsion can be obtained by heating an oil-in-water type emulsion comprising L-menthol, a fat or oil and a surfactant at 60° C. or higher.

2 Claims, No Drawings

SMOOTH MUSCLE PERISTOLE INHIBITOR

This application is a U.S. national stage of International Application No. PCT/JP03/06304 filed May 20, 2003.

FIELD OF THE INVENTION

The present invention relates to an L-menthol-containing smooth muscle contraction inhibitor having an improved transparency and comprising of an emulsion which is stable for a prolonged period.

BACKGROUND OF THE INVENTION

A contraction or peristalsis of a smooth muscle for example of a digestive tract prevents a correct diagnosis upon an endoscopic test of a digestive tract such as a stomach or large intestine and allows a minute lesion such as a small-sized carcinoma to be missed.

As an anti-spasmodic agent upon an endoscopic test of a digestive tract, an anti-cholinergic agent scopolamine butylbromide (Trade name: Buscopan Injection, Nippon Boehringer Ingelheim Co., Ltd.) or glucagon has conventionally been prescribed. However, the scopolamine butylbromide is contraindicated in a patient having glaucoma, prostatic hypertrophy, arrhythmia and the like, and glucagon has a problematically low ability of inhibiting a gastric contraction.

In addition, some of these formulations involves a risk of causing ophthalmic regulatory failure or vertigo upon administration, and poses a problem in an individual receiving these formulations upon an endoscopic test because the individual should refrain for example from driving a car for a while after completion of the test.

Accordingly, in an attempt to solve the problems mentioned above, an investigation was made recently to produce a digestive tract contraction inhibitor using a peppermint oil whose main ingredient is L-menthol having a digestive tract contraction-inhibiting effect (GASTROINTESTINAL ENDOSCOPY, Vol. 53, No. 2, 172-177 (2001)). Nevertheless, a conventional formulation, which has been proposed to produce by mixing and stirring a peppermint oil and water in the presence of an homogenizer followed by allowing to stand at room temperature for a period of about one day and removing the oily component floating on the surface of the liquid to collect only a solubilized part, or by mixing and stirring a peppermint oil and water in the presence of an homogenizer followed by allowing to stand at room temperature for a period of 24 hours and then filtering the aqueous layer to remove the oily component, may allow a highly volatile L-menthol as a main ingredient of the peppermint oil to be evaporated off when allowed to stand at room temperature for several hours or longer after completion of the formulation, resulting in a reduced content, which may lead to a problematic non-uniform L-menthol content upon administration to patients. Accordingly, a constant amount of a conventionally-formulated product may fail to provide a constant effect even when administered for example by spraying as a gastric contraction inhibitor onto the inner wall of a stomach, resulting in an insufficient inhibitory effect on the contraction.

Furthermore, any of these products requires a preparation just before use because of a difficulty in storing for a prolonged period after the formulation, and such a preparation is difficult practically at each stage of the clinical medicine.

We had previously developed a digestive tract contraction inhibitor in an oil-in-water form exhibiting no L-menthol precipitation even after a prolonged storage by emulsifying the L-menthol as a main ingredient of a peppermint oil together with a fatty acid and/or a fat or oil using a surfactant. Nevertheless, some of these formulations is turbid, and such a turbid emulsion is concentrated onto a recess, groove or wrinkle, if any, on the surface of a digestive tract, when sprayed over such an inner wall, resulting in a problematic difficulty in observing a bottom or deeper end.

Under such a circumstance, development of a digestive tract contraction inhibitor having a reduced L-menthol volatility and an improved transparency, i.e., improved light transmittance, and also consisting of an emulsion which is stable for a prolonged period is highly desired.

SUMMARY OF THE INVENTION

We made an effort to obtain an L-menthol-containing smooth muscle contraction inhibitor, especially a digestive tract contraction inhibitor which is stable for a prolonged period, less volatile, exhibits a reduced volatility of the L-menthol, and also exhibits a high light transmittance, and finally discovered that by mixing L-menthol, a fat or oil, surfactant and water followed by heating the emulsion at any stage of the manufacturing process an L-menthol-containing emulsion can be obtained which has an average particle size as small as less than 100 nm, which exhibits a high liquid light transmittance, which has a reduced L-menthol volatility, and which is stable for a prolonged period. This emulsion was almost transparent, and posed no problem upon an endoscopic examination even when a fluid is retained in a recess, groove or wrinkle on a gastric inner wall over which it was sprayed. We made an additional effort based on the findings discussed above, and finally established the present invention.

Thus, the invention is:

(1) a smooth muscle contraction inhibitor having an improved light transmittance which comprises an emulsion containing L-menthol, a fat or oil and a surfactant and having an average oil particle size of less than 100 nm, (2) the smooth muscle contraction inhibitor according to the above-mentioned (1), wherein the light transmittance rate of the emulsion is 50% or more, (3) the smooth muscle contraction inhibitor according to the above-mentioned (1) or (2), wherein 0.01 to 5% by weight of the L-menthol based on the entire emulsion, 0.5 to 10-fold weight of the fat or oil based on the L-menthol and 0.1 to 10-fold weight of the surfactant based on the total weight of the L-menthol and the fat or oil, (4) the smooth muscle contraction inhibitor according to the above-mentioned (1), wherein the fat or oil is at least one selected from monoglycerides, diglycerides and triglycerides of fatty acids, (5) the smooth muscle contraction inhibitor according to the above-mentioned (1), wherein the fat or oil is at least one selected from medium chain triglycrides (MCT), soybean oil, rapeseed oil, safflower oil, corn oil, palm oil, olive oil, peanut oil, sesame oil and cottonseed oil, (6) the smooth muscle contraction inhibitor according to the above-mentioned (1), wherein the surfactant is a polyoxyethylene hydrogenated castor oil, (7) a method for producing a smooth muscle contraction inhibitor with an improved light transmittance rate having an average oil particle size of less than 100 nm which comprises heating an emulsion containing L-menthol, a fat or oil and a surfactant at 60° C. or higher, (8) a method for inhibiting a smooth muscle contraction comprising contacting an emulsion, containing L-menthol, a fat or oil and a surfactant, having an average oil particle size of less than 100 nm and also having an improved light transmittance, with an inner surface of the smooth muscle, (9) the method for inhibiting a smooth muscle contraction according to the above-mentioned (8), wherein the light transmittance rate of the emulsion is 50% or more,

(10) the method for inhibiting a smooth muscle contraction according to the above-mentioned (8), wherein the emulsion is one comprising 0.01 to 5% by weight of the L-menthol based on the entire emulsion, 0.5 to 10-fold weight of the fat or oil based on the L-menthol and 0.1 to 10-fold weight of the surfactant based on the total weight of the L-menthol and the fat or oil,

(11) use of an emulsion comprising L-menthol, a fat or oil and a surfactant and having an average oil particle size of less than 100 nm for producing a smooth muscle contraction inhibitor whose light transmittance rate is improved,

(12) the use according to the above-mentioned (11), wherein the light transmittance rate of the emulsion is 50% or more, and

(13) the use according to the above-mentioned (11), wherein the emulsion is one comprising 0.01 to 5% by weight of the L-menthol, 0.5 to 10-fold weight of the fat or oil based on the L-menthol and 0.1 to 10-fold weight of the surfactant based on the total weight of the L-menthol and the fat or oil.

The L-menthol employed in the present invention is a main component of a peppermint oil or mentha oil contained therein in an amount usually of 30% by weight or more, which is obtained by steam distillation of a plant for example of Mentha piperita or Mentha arvensis. While an L-menthol containing material may be a peppermint oil or mentha oil as it is, such a peppermint oil or mentha oil may further be subjected for example to a fractional distillation to obtain a highly purified one, which can also be employed preferably. It is especially preferred to use one as highly pure as one having an L-menthol content of 90% by weight or higher. Recently, a synthetic product is also employed. In any way, one in compliance with the Japanese Pharmacopoeia standard of L-menthol may be preferably employed.

In the present invention, the L-menthol is present in an amount of 0.01 to 5% by weight, preferably 0.1 to 3% by weight, more preferably 0.3 to 1.5% by weight based on the entire amount of the emulsion.

The fat or oil employed in the present invention is not limited particularly as long as it is a fat or oil which can be employed in a pharmaceutical product, and is preferably a medium chain fatty acid triglyceride (MCT) as well as a long chain fatty acid triglyceride (LCT) such as a soybean oil, olive oil, palm oil and the like.

As the MCT, one having 6 to 12 carbon atoms in its fatty acid moiety may be employed, and a mixture of those having different carbon numbers can also be employed (e.g., "Panasate 800" from NOF Corp., "Coconard RT" from Kao Corp.) may also be employed.

Such a fat or oil may be employed as a solvent for the L-menthol, in an amount of 0.5 to 10-fold weight, preferably 1 to 5-fold weight based on the L-menthol. The fat or oil can be employed usually in an amount of 0.1 to 5% by weight, preferably 0.5 to 3% by weight based on the entire weight of the emulsion.

The surfactant employed in the invention is not limited particularly as long as it is a surfactant which can be employed in a pharmaceutical product, and is preferably a polyoxyethylene hydrogenated castor oil, sucrose fatty acid ester, polysorbate and the like. It is a matter of course that a mixture of these surfactants can be employed. Among those listed above, a polyoxyethylene hydrogenated castor oil is employed preferably.

The amount of the surfactant based on the total weight of the L-menthol and the fat or oil may vary depending on the type of the surfactant, and may usually be 0.1 to 10-fold weight, preferably 0.5 to 5.0-fold weight. This surfactant is employed usually in an amount of 0.1 to 20% by weight, preferably 0.5 to 15% by weight based on the entire weight of the emulsion.

It is also possible to employ, in addition to the surfactant mentioned above, another pharmaceutically acceptable surfactant, for example, an edible nonionic surfactant. An emulsion of the present invention can be obtained by stirring a water containing the L-menthol, the fat or oil and the surfactant mentioned above while heating or by heating after stirring or mixing of the water.

As used herein, a heat treatment can be accomplished by a method which is not limited specifically, and it is acceptable to heat an L-menthol-containing emulsion which contains the L-menthol, a fat or oil and a surfactant at any stage during the course of the manufacturing. An example of the heat treatment may be a procedure in which the emulsification of a mixture is conducted for example by a homomixer under a heating condition, or in which the emulsification of a mixture is conducted using a high pressure homogenizer under a heating condition, in which an emulsion is filled in a contained which is then sterilized by heating, in which an emulsion is filled in a container which is then stored at a high temperature, or in which the emulsification was conducted with heating followed by a sterilization also by heating. While the heating time may vary depending on the stirring condition, the heating condition is maintained for 1 minute to 14 days, preferably 5 minutes to 6 hours.

The heating temperature may be 60° C. or higher, preferably 70° C. to 130° C., especially 80° C. to 121° C. By conducting the heating sterilization under a heating condition for an ordinary lipid emulsion (110 to 121° C.), a satisfactory result is obtained.

The emulsion as the smooth muscle contraction inhibitor of this invention thus obtained has an average particle size of less than 100 nm, preferably 70 nm or less, more preferably 50 nm or less.

The measurement of the average particle size was conducted by placing 0.1 ml of a sample in a 10-mm cell and adding a distilled water to obtain a sample solution which was measured using a light scattering photometer (ELS8000, OTSUKA ELECTRONICS CO., LTD.). When the concentration of an emulsion was too low or high, then the measurement was conducted after adding or diluting the sample.

A conventional emulsion having a large average particle size undergoes a reduction in the L-menthol content of the fluid during storage, resulting in a problematically variation in the quality, and tends to be turbid, resulting in a problematic difficulty in identifying a lesion when being sprayed onto the lesion upon an endoscopic examination for example of a digestive tract. On the other hand, the emulsion of the present invention is transparent or slightly white because of its extremely fine oil particle, has a high light transmittance, and can prevent the L-menthol content from being reduced during storage due to the use of an oil or fat, whereby avoiding the problems mentioned above.

The light transmittance of an inventive emulsion is preferably 50% or higher, more preferably 70% or higher, most preferably 90% or higher.

The measurement of the light transmittance was conducted by placing a sample solution in a 10-mm cell that was subjected to a double beam spectrophotometer Model U-2001 (HITACHI, LTD.) at 900 nm as a measurement wavelength.

The emulsion of this invention can be obtained by means of a combination of a known emulsification or solubilization with a heating of the liquid. A preferred method is one of those listed below, to which it is not limited.

[1] First, L-menthol is dissolved in a fat or oil. The dissolution may be conducted at room temperature or with heating. Then, the resultant uniform mixture of the L-menthol and the fat or oil is added to a dispersion of water containing a surfactant which has been obtained by stirring for example by a homomixer, and the mixture is stirred thoroughly using a stirrer such as a homomixer. If necessary, a further ultrasonication or the use of a high-pressure homogenizer may be conducted to ensure a uniform and fine particle of the emulsion. Thereafter, the emulsion thus prepared is sterilized by an autoclave at 115° C. for 5 to 30 minutes.

[2] An emulsion is prepared by the method described above, and the heating is conducted at about 60° C. instead of the autoclave sterilization, for a storage period of about 1 week.

[3] A surfactant is added to water and dispersed using a stirrer such as a homomixer, and thereafter L-menthol and a fat or oil is added and the mixture is stirred at 80° C. or higher for 10 minutes or more by a homomixer.

An emulsion may also appropriately contain if necessary other active ingredients, as well as thickening agent, stabilizer, preservative, antifoam agent and the like.

A thickening agent may for example be a carrageenan, methyl cellulose, carboxymethyl cellulose, guar gum, pectin and the like. By adding such a thickening agent, the falling-down rate of the emulsion after sprayed over the inner wall of a digestive tract can appropriately be adjusted, The amount of the thickening agent may vary depending on the type of the thickening agent, and it is usually 0.01 to 5% by weight based on the emulsion.

The stabilizer may for example be sodium edentate, the preservative may for example be sorbic acid, benzalkonium chloride, paraben and the like, and the antifoam agent may for example be a silicone oil such as dimethylpolysiloxane, each of which may be added in an appropriate amount.

The site to which the present smooth muscle contraction inhibitor may for example be a smooth muscle of a digestive tract such as esophagus, stomach, duodenum, bile duct, small intestine, large intestine, colon, rectum and the like. The present contraction-inhibiting emulsion can be employed for example upon laparotomic or endoscopic surgery of a digestive tract, or upon endoscopic observation of a digestive tract or also upon any medical care requiring the inhibition of the smooth muscle contraction of a digestive tract, by spraying it directly onto the inner side of the digestive tract via a spray or an endoscopic forceps channel, or by filling it in a digestive organ such as stomach or intestine via a tube, whereby bringing the emulsion into contact with the smooth muscle. When directly administering a certain amount of the emulsion via the spray or the endoscopic forceps channel, it is preferable to fill a unit dose of the emulsion which had been prepared as described above into an extrusive vessel such as a pre-filled syringe. It is a matter of course that an present product can be filled and stored in a container such as a vial or ampoule.

BEST MODE FOR CARRYING OUT THE INVENTION

The invention is further described in the following Examples.

Example 1

1.12 g of L-menthol (L-Menthol, The SUZUKI Menthol CO., LTD.) and 2.8 g of an MCT (Coconard RT, KAO CORP.) were mixed and dissolved in a water bath at 60° C. to obtain an L-menthol solution. 0.28 g of Polysorbate 80 (Rheodol TW-0120V, KAO CORP.), 2.1 g of sucrose fatty acid ester (SURFHOPE J1616, MITSUBISHI-KAGAKU FOODS CORP.) and 4.2 g of HCO-60 (NIKKOL HCO-60, NIKKO CHEMICALS CO., LTD.) were combined with 60 ml of water, and dispersed by a homomixer. To this fluid, the L-menthol was added and emulsified by a homomixer (POLYTRON PT 1000, KINEMATICA CORP.). Then, the fluid was combined with water to make the entire volume 140 ml, which was further emulsified by an ultrasonic homogenizer (SINIHIER 250, BRANSON SONIC POWER COMPANY) for 10 minutes, to obtain an emulsion. Then, this emulsion was sterilized by an autoclave for 20 minutes at 115° C. to obtain a desired emulsion. The average particle size of this emulsion was measured by a particle size meter (ELS 8000, OTSUKA DENSHI CO., LTD.), which revealed that the average particle size was 25.9 nm.

Example 2

1.12 g of L-menthol (L-Menthol, The SUZUKI Menthol CO., LTD.) and 2.8 g of an MCT (Coconard RT, KAO CORP.) were mixed and dissolved in a water bath at 60° C. to obtain an L-menthol solution. 0.28 g of Polysorbate 80 (Rheodol TW-0120V, KAO CORP.), 1.68 g of sucrose fatty acid ester (SURFHOPE J1616, MITSUBISHI-KAGAKU FOODS CORP.) and 2.8 g of HCO-60 (NIKKOL HCO-60, NIKKO CHEMICALS CO., LTD.) were combined with 60 ml of water, and dispersed by a homomixer. To this fluid, the L-menthol was added and emulsified by a homomixer. Then, the fluid was combined with water to make the entire volume 140 ml, which was further emulsified by an ultrasonication for 10 minutes to obtain an emulsion. Then, this emulsion was sterilized by an autoclave for 20 minutes at 115° C. to obtain an desired emulsion. The average particle size of this emulsion was 30.3 nm.

Example 3

4.0 g of Polysorbate 80 (Rheodol TW-0120V, KAO CORP.), 24.0 g of sucrose fatty acid ester (SURFHOPE J1616, MITSUBISHI-KAGAKU FOODS CORP.) and 40.0 g of HCO-60 (NIKKOL HCO-60, NIKKO CHEMICALS CO., LTD.) were combined with 1600 ml of water, and dispersed by a homomixer. To this fluid, 40.0 g of an MCT (Coconard RT, KAO CORP.) and 16.0 g of L-menthol (L-Menthol, The SUZUKI Menthol CO., LTD.) were added, and emulsified at 80° C. by a homomixer for 10 minute. Then, the fluid was combined with water to make the entire volume 2000 ml to obtain an intended emulsion. The average particle size of this emulsion was 29.7 nm.

Example 4

4.0 g of Polysorbate 80 (Rheodol TW-0120V, KAO CORP.), 20.0 g of sucrose fatty acid ester (SURFHOPE J1616, MITSUBISHI-KAGAKU FOODS CORP.) and 36.0 g of HCO-60 (NIKKOL HCO-60, NIKKO CHEMICALS CO., LTD.) were combined with 1600 ml of water, and dispersed by a homomixer. To this fluid, 40.0 g of an MCT (Coconard RT, KAO CORP.) and 16.0 g of L-menthol (L-Menthol, The SUZUKI Menthol CO., LTD.) were added, and emulsified at 80° C. by a homomixer for 10 minute. Then, the fluid was combined with water to make the entire volume 2000 ml to obtain a desired emulsion. The average particle size of this emulsion was 32.3 nm.

Comparative Example 1

0.28 g of Polysorbate 80 (Rheodol TW-0120V, KAO CORP.), 2.1 g of sucrose fatty acid ester (SURFHOPE J1616, MITSUBISHI-KAGAKU FOODS CORP.) and 4.2 g of HCO-60 (NIKKOL HCO-60, NIKKO CHEMICALS CO., LTD.) were combined with 60 ml of water, and dispersed by a homomixer. To this fluid, 2.80 g of an MCT (Coconard RT, KAO CORP.) and 1.12 g of L-menthol (L-Menthol, The SUZUKI Menthol CO., LTD.) were added, and emulsified at room temperature (formulation temperature upon initiation of the emulsification: 22.7° C.) using a homomixer. Then, the fluid was combined with water to make the entire volume 140 ml to obtain an emulsion. The average particle size of this emulsion was 2075.4 nm.

Comparative Example 2

0.28 g of Polysorbate 80 (Rheodol TW-0120V, KAO CORP.), 1.68 g of sucrose fatty acid ester (SURFHOPE J1616, MITSUBISHI-KAGAKU FOODS CORP.) and 2.8 g of HCO-60 (NIKKOL HCO-60, NIKKO CHEMICALS CO., LTD.) were combined with 60 ml of water, and dispersed by a homomixer. To this fluid, 2.80 g of an MCT (Coconard RT, KAO CORP.) and 1.12 g of L-menthol (L-Menthol, The SUZUKI Menthol CO., LTD.) were added, and emulsified at room temperature (formulation temperature upon initiation of the emulsification: 23.2° C.) using a homomixer. Then, the fluid was combined with water to make the entire volume 140 ml to obtain an emulsion. The average particle size of this emulsion was 8911.6 nm.

Comparative Example 3

16 g of L-menthol (L-Menthol, The SUZUKI Menthol CO., LTD.) and 16 g of a propylene glycol fatty acid ester (RIKEMAL PO-100, RIKEN VITAMIN CO., LTD.) were mixed and dissolved on a water bath at 60° C. to obtain an L-menthol solution. 6 g of Polysorbate 80 (IONET T-80PA, SANYO CHEMICAL INDUSTRIES, LTD.) and 6 g of glycerin fatty acid ester (EXCEL P-40S, KAO CORP.) were combined with 1600 ml of water, and dispersed by a homomixer. To this fluid, the L-menthol solution was added and emulsified at 60° C. for 10 minutes by a homomixer. Then, the fluid was combined with water to make the entire volume 1920 ml, which was further emulsified 5 times using a high-pressure homogenizer (310 bar) to obtain an emulsion.

The same procedure was repeated again to produce the same formulation, and the 1st and the 2nd formulations were combined to make the entire volume 4000 ml, whereby obtaining an intended emulsion. The average particle size of this emulsion was 148.7 nm.

Experimental Example 1

Each 20 ml of the emulsions obtained in Examples 1 to 4 and Comparative Examples 1 and 2 was placed in a 20-ml vial and stored at 20° C. for 1 month, and then examined for the average particle size, the light transmittance (%) and the appearance. The results are shown in Table 1 together with their respective initial values.

The light transmittance was measured by placing a sample in a 10-mm cell of a double beam spectrophotometer Model U-2001 (HITACHI, LTD.) set at 900 nm as a measurement wavelength.

TABLE 1

| Example or Comparative Example | Immediately after preparation | | | After storage for one month at room temperature (20° C.) | | |
|---|---|---|---|---|---|---|
| | Average particle size (nm) | Light transmittance (%) | Appearance | Average particle size (nm) | Light transmittance (%) | Appearance |
| Example 1 | 25.9 | 97.21 | Slightly bluish white and transparent | 25.1 | 96.82 | Slightly bluish white and transparent |
| Example 2 | 30.3 | 97.48 | Slightly bluish white and transparent | 29.5 | 96.21 | Slightly bluish white and transparent |
| Example 3 | 29.7 | 97.48 | Slightly bluish white and transparent | 34.5 | 94.68 | Slightly bluish white and transparent |
| Example 4 | 32.3 | 95.63 | Slightly bluish white and transparent | 48.1 | 90.06 | Slightly bluish white and transparent |
| Comparative Example 1 | 2075.4 | 0.00 | White, Opaque | — | — | — |
| Comparative Example 2 | 8911.6 | 0.02 | White, Opaque | — | — | — |

As evident from Table 1, each emulsion obtained in Examples 1 to 4 exhibited a high light transmittance not only just after preparation but also after storage for 1 month at room temperature, being almost transparent. On the other hand, each emulsion obtained in Comparative Examples 1 and 2 was white and opaque even just after preparation, with its light transmittance being zero or almost zero.

Experimental Example 2

Each 20 ml of the emulsions obtained in Example 2 and Comparative Example 3 described above was placed in a 20-ml capacity of vessel made of polypropyrene and stored at 25° C. for 1 month, and then examined for the residual rate of L-menthol. The results are shown in Table 2 together with their respective initial values.

The residual rate of L-menthol was measured in accordance with the menthol assay of menthol oil prescribed in Japanese Pharmacopoeia by a gas chromatography (Gas Chromatograph Model GC-14A, Shimadzu Corp.).

TABLE 2

| Example or Comparative Example | Immediately after preparation | | | After storage for one month at room temperature (25° C.) |
|---|---|---|---|---|
| | Average particle size (nm) | Appearance | Residual rate of L-menthol | Residual rate of L-menthol |
| Example 1 | 25.9 | Slightly bluish white and transparent | 100 | 99.1 |
| Comparative Example 3 | 148.7 | Slightly bluish white and transparent | 100 | 93.3 |

As evident from Table 2, the emulsion obtained in Example 2 (average particle size: 25.9 nm) exhibited a residual rate of L-menthol as extremely high as 99.1% even after storage for 1 month, while the emulsion obtained in Comparative Example 3 (average particle size: 148.7 nm) exhibited a residual rate of L-menthol as rather low as 93.3%.

Experimental Example 3

Effect of L-menthol on gastric contraction in anesthetized dog
Materials and Methods for Testing Each dog fasting one whole day and night (weighing about 10 kg) received atropine sulfate as a pre-anesthesia drug intravenously followed by intravenous sodium thiopental to effect the anesthesia. An intratracheal tube was inserted and fixed. A gas mixture of nitrous oxide and oxygen was introduced. Using an isoflurane vaporizer the isoflurane was introduced. The concentration of the isoflurane was increased gradually from 0.5%, whereby maintaining the anesthesia.

This anesthetized dog was fixed in a recumbent position on the left and a gastric endoscopy was conducted by a standard method. Then, 10 ml of the emulsion prepared in Example 2 which had been stored for 1 month after preparation was sprayed onto the pylorus region via the endoscopic forceps channel, and then 10 ml of air was flushed immediately to extrude the emulsion remaining in the forceps channel. The time period from the administration of the emulsion through the discontinuation of the pylorus contraction was measured, and the results were represented in Table 3 shown below. Since the sprayed fluid was almost transparent in any case, there was no problem in the endoscopic observation after spraying onto the inner wall of the stomach.

TABLE 3

| Administered emulsion | Animal number | Time period until contraction discontinuation | Duration of contraction discontinuation |
|---|---|---|---|
| Example 2 | 1 | 62 seconds | 12 minutes |
| | 2 | 55 seconds | 16 minutes |
| | 3 | 63 seconds | 15 minutes |
| Non-treatment group | 1 | No contraction inhibition was observed | No contraction inhibition was observed |
| | 2 | No contraction inhibition was observed | No contraction inhibition was observed |

As evident from Table 3, the inventive emulsions were proven to be able to discontinue the digestive contraction within a short time period, and the discontinuation of the contraction was maintained over an extremely appropriate time period for the examination.

INDUSTRIAL APPLICABILITY

The liquid smooth muscle contraction inhibitors according to the invention have an improved liquid transparency, avoid the volatilization of the L-menthol, and are stable over a prolonged period even when stored at ordinary temperature (25° C.). Accordingly, they can preferably be employed for inhibiting a digestive tract contraction transiently for example upon an endoscopic examination of the digestive tract.

The invention claimed is:
1. A smooth muscle contraction inhibitor of a digestive tract having an improved light transmittance rate which comprises an emulsion comprising
   (a) 0.1 to 3% by weight of L-menthol based on the entire emulsion,
   (b) 0.5 to 3% by weight of a triglyceride of fatty acids based on the entire emulsion, and
   (c) 0.1 to 20% by weight of a surfactant consisting of a polyoxyethylene hydrogenated castor oil, sucrose fatty acid ester and polysorbate based on the entire emulsion,
and having an average oil particle size of less than 100 nm and the light transmittance rate of 70% or more.
2. The smooth muscle contraction inhibitor of a digestive tract according to claim 1, wherein the triglyceride of fatty acids is medium chain triglycerides (MCT), and/or at least one triglyceride of an oil selected from the group consisting of soybean oil, rapeseed oil, safflower oil, corn oil, palm oil, olive oil, peanut oil, sesame oil and cottonseed oil.

* * * * *